(12) United States Patent
Hsu

(10) Patent No.: US 7,588,776 B2
(45) Date of Patent: *Sep. 15, 2009

(54) **PHARMACEUTICAL USE OF WATER-SOLUBLE FRACTION OF *GRAPTOPETALUM***

(76) Inventor: Shih-Lan Hsu, #3, 8F-5, Sec. 3, Sin-Hai Road Da-an District, Taipei 106 (TW)

( * ) Notice: Subject to any disclaimer, the term of this patent is extended or adjusted under 35 U.S.C. 154(b) by 10 days.

This patent is subject to a terminal disclaimer.

(21) Appl. No.: 12/038,132

(22) Filed: Feb. 27, 2008

(65) Prior Publication Data

US 2008/0160112 A1     Jul. 3, 2008

Related U.S. Application Data

(63) Continuation-in-part of application No. 10/931,791, filed on Aug. 31, 2004, now Pat. No. 7,364,758.

(51) Int. Cl.
    *A01N 65/00* (2006.01)
    *A61K 36/00* (2006.01)
(52) U.S. Cl. .................. 424/425; 424/769; 514/838; 514/893; 514/894
(58) Field of Classification Search .................. None
    See application file for complete search history.

(56) References Cited

U.S. PATENT DOCUMENTS

| 4,996,200 | A | 2/1991 | Nishimura et al. |
| 5,911,993 | A | 6/1999 | Jian et al. |
| 7,364,758 | B2 * | 4/2008 | Hsu |
| 2004/0023909 | A1 | 2/2004 | Roy-Chowdhury et al. |

FOREIGN PATENT DOCUMENTS

| CN | 1355254 | 6/2002 |
| JP | 04208223 | 7/1992 |
| JP | 2004026768 | 1/2004 |
| WO | WO02/05830 | 1/2002 |

OTHER PUBLICATIONS

Foroncewicz et al., Transplantion Proceedings (2003), 35(6): 2310-2312. Anti-CD25 and tacrolimus therapy may not prevent early primary biliary cirrhosis: recurrence after liver transplantation: Two case reports.
Bach et al., The Mount Sinai Journal of Medicine (Sep. 2003), 70(4): 242-250. Primary biliary cirrhosis: A Mount Sinai perspective.
PTO 06-4732, Translation of Chinese Patent CN 1355254 A: "*Echevaria glauca* Polysaccharides [Shilianhua Duotang]" by Ding Qing. Translated by: Schreiber Translations, Inc. (Jun. 2006).
Worman., Cirrhosis: What is Cirrhosis?. http://cpmcnet.columbia.edu/dept/gi/cirrhosis.html downloaded May 16, 2006.
Ul, Wayback Machine: http://web.archive.org/web*/http://cpmcnet.columbia.edu/dept/gi/cirrhosis.html downloaded Aug. 6, 2006.
Arai, et al., (2001). Effect of herb supplement on hepatic enzyme activities in ddY mice. Lab Anim. 35(3): 288-291.
Chou et al., Antimutagenic potential of *Graptopetalum paraquayense* E. Walther. 2004 Institute of Food Technologists Annual Meeting. Jul. 12-16, 2004, Session 114F, abstract 4, [retrieved Dec. 6, 2005]. Retrieved from the Internet: URL:http://ift.confex.com/ift/techprogram/paper_22911.htm, whole document.
Chung et al., (2005). Studies on the antioxidative activity of *Graptopetalum paraguayense* E. Walther. Food Chemistry 91:419-424.
Hsieh et al., (2005). Inhibitory effect of some selected nutraceutic herbs on LDL glycation induced by glucose and glyoxal. J Ethnopharmacol. 102(3):357-363.
Huang et al., (2005). Studies on the inhibitory effect of *Graptopetalum paraguayense* E. Walther extracts on mushroom tyrosinase. Food Chemistry 89:583-587.
Kang et al., (2000). Antiproliferative effects of alkaloids from *Sedum sarmentosum* on murine and human hepatoma cell lines. J Ethnopharmacol. 70(2):177-182.
Wu et al., (2003). Effect of compound rhodiola sachalinensis A Bor on $CCl_4$-induced liver fibrosis in rats and its probable molecular mechanisms. World J Gastroenterol. 9(7):1559-1562.
Desmet et al., (1994). Classification of chronic hepatitis: diagnosis, grading and staging. *Hepatology* 19(6):1513-1520.
Friedman., (1993). The cellular basis of hepatic fibrosis. Mechanism and treatment strategies. *N. Engl J Med.* 328(25):1828-1835.
Giladi et al., (2003). Small interfering RNA inhibits hepatitis B virus replication in mice. *Mol Ther*. 8(5):769-776.
Pines et al., (1997). Halofuginone, a specific inhibitor of collagen type I synthesis, prevents dimethylnitrosamine-induced liver cirrhosis. *J Hepatol*. 27(2):391-398.
Saller et al., (2001). The use of silymarin in the treatment of liver diseases. *Drugs*. 61(14):2035-2063.
Chung et al. "Studies on the antioxidative activity of *Graptopetalum paraguayense* E. Walther", IFT Annual Meeting, Jul. 12-16, 2004, Las Vegas, Abstract 9, 1 page.

\* cited by examiner

*Primary Examiner*—Michele C. Flood
(74) *Attorney, Agent, or Firm*—Occhiuti Rohlicek & Tsao LLP

(57) ABSTRACT

A pharmaceutical composition containing a water-soluble fraction of *Graptopetalum* and its use in treating a liver disease or condition, such as inflammation, steatosis, and fibrosis.

19 Claims, 7 Drawing Sheets (A)

(B)

(A)

(B)

PHARMACEUTICAL USE OF WATER-SOLUBLE FRACTION OF *GRAPTOPETALUM*

CROSS-REFERENCE TO RELATED APPLICATIONS

This application is a continuation-in-part application of U.S. application Ser. No. 10/931,791, filed Aug. 31, 2004, the contents of which are incorporated herein by reference in its entirety.

FIELD OF THE INVENTION

The present invention relates to the therapeutic and prophylactic effects of a water-soluble fraction of *Graptopetalum* on liver-related diseases and medical conditions.

BACKGROUND OF THE INVENTION

The liver is a multi-functional organ. Its basic functions can be divided into three categories: (1) the vascular functions for storage and filtration of blood, (2) the metabolic functions which are involved with most of the metabolic systems of the body, and (3) the secretory and excretory functions responsible for bile formation. Major activities of the liver include detoxification and elimination of both endogenous and exogenous toxins, deamination of amino acids and formation of urea, regulation of blood sugar through the formation of glycogen, production of plasma proteins, production and secretion of bile, and phagocytosis of particulate matter from the splanchnic (intestinal) circulation.

As a result of liver's many different roles, when the liver is damaged, its various functions are disturbed simultaneously in different combinations, depending on the nature and location of the damage. Liver damage from any source may result in liver regeneration, necrosis (cell death), degeneration, inflammation, fibrosis, or combinations of these processes. Although the liver has great functional reserves, with progressive injury, disruption of liver function can have life-threatening consequences. Cirrhosis, which is a common end-stage liver disease, is one of the top ten causes of death in the Western world.

Despite the significance and potential severity of liver disease, therapeutic approaches are limited. Many types of liver disease are the result of viruses (e.g., hepatitis A, B, C, D, and E), and effective anti-viral therapies are rare and often cause potentially severe side effects. Other liver diseases are the results of previous toxic exposure (such as alcoholic cirrhosis and exposure to toxic plants, or environmental pollutants). In still other cases, liver diseases are the result of poorly understood interplay of various factors, including genetic factors, environmental conditions, and immune system activity (autoimmune hepatitis). No matter what the causes are, therapeutic approaches to liver diseases are complicated by two factors. Since the liver is responsible for detoxification, any use of drugs may increase the burden upon the liver and lead to deterioration of the condition. Furthermore, liver fibrosis, which occurs in many liver diseases and conditions, is generally an irreversible process. Consequently, the usable portion of the liver decreases with the progress of fibrosis, resulting in increasing complications of other organs that rely on liver functions.

Therefore, a pharmaceutical agent for the liver should ideally prevent fibrosis from occurring or progressing. In addition, it is also desirable if the agent does not pose a metabolic burden on the liver, as well as has few or no side effects.

The details of one or more embodiments of the invention are set forth in the description below. Other features or advantages of the present invention will be apparent from the following drawings and detailed description of several embodiments, and also from the appending claims.

BRIEF SUMMARY OF THE INVENTION

The present invention provides, inter alia, compositions that comprise a water-soluble fraction of *Graptopetalum* as an active ingredient. The inventors discovered that this common plant can protect animals from a toxic substance that causes inflammation and fibrosis of the liver, weight loss, spleen swelling, and ultimately death. With the administration of the water-soluble fraction of *Graptopetalum*, inflammation and fibrosis were significantly inhibited; body weight, liver weight, and spleen weight of the animals were nearly normal; and the survival rate was greatly improved. In particular, the water-soluble fraction of *Graptopetalum* inhibits proliferation of activated hepatic stellate cells, which play a pivotal role in liver fibrosis. Consistent with this observation, the water-soluble fraction of *Graptopetalum* also inhibits the accumulation of collagen and prevents fibrosis to occur or progress. In addition, the water-soluble fraction of *Graptopetalum*, even at a high dosage, displayed no detectable side effects on normal hepatocytes.

Accordingly, one aspect of the present invention provides a pharmaceutical composition comprising a water-soluble fraction of *Graptopetalum*. The *Graptopetalum* can be any *Graptopetalum* species, e.g., *Graptopetalum paraguayense*.

The pharmaceutical composition may further comprise a pharmaceutically acceptable excipient or carrier. The pharmaceutical composition may also comprise at least one other agent, particularly an agent that has anti-inflammatory, anti-steatosis, anti-viral, or anti-fibrosis activities. For example, the agent may be selected from the group consisting of arbutin, lemon extract, cucumber extract, mercaptosuccinic acid, mercaptodextran, kojic acid, derivatives of kojic acid, vitamin C, hydroquinone, glutathione, cysteine, mulberry extract, licorice extract, and bearberry extract.

The pharmaceutical composition may be formulated for any suitable route of administration, preferably oral or topical administration.

Another aspect of the present invention is a method of preventing or treating a liver disease or medical condition by administering (e.g., orally) to a subject an effective amount of the pharmaceutical composition described herein. A subject who needs this treatment either suffers from or is susceptible to a liver disease or a liver medical condition, including liver inflammation, liver steatosis, liver fibrosis, liver cirrhosis, and hepatitis B. In one example, the pharmaceutical composition used in this method contains an aqueous *Graptopetalum* extract prepared by freeze drying a whole *Graptopetalum* plant, grinding the dried plant to form *Graptopetalum* powder, lyophilizing the powder, extracting the lyophilized powder with water (e.g., twice) to obtain an aqueous *Graptopetalum* extract, and finally lyophilizing the extract.

Another aspect of the present invention provides a method for inhibiting hepatic stellate cell proliferation, comprising contacting hepatic stellate cells with the pharmaceutical composition comprising a water-soluble fraction of *Graptopetalum*. Yet another aspect of the present invention provides a method for selectively killing hepatic stellate cells, comprising contacting hepatic stellate cells with the pharmaceutical composition comprising a water-soluble fraction of *Graptopetalum*. The hepatic stellate cells are preferably located in a mammal, and most preferably in a human.

BRIEF DESCRIPTION OF DRAWINGS

The patent or application file contains at least one drawing executed in color. Copies of this patent or patent application publication with color drawings will be provided by the Office upon request and payment of the necessary fee.

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the Drawings:

FIG. 1 shows the number of surviving rats in each of the following groups: the normal group (Control), the treatment group (dimethylnitrosamine (DMN)+ZC008 W, wherein "ZC008 W" refers to the aqueous *Graptopetalum* extract), the positive control group (DMN+Silymarin), and the negative control group (DMN).

FIG. 2 shows the photographs of the liver and spleen of rats from each of the following groups: the normal group (Control), the treatment group (DMN+ZC008 W, wherein "ZC008 W" refers to the aqueous *Graptopetalum* extract), the positive control group (DMN+Silymarin), and the negative control group (DMN).

FIG. 3 shows the microscopic photographs of liver tissues, stained with hematoxylin and eosin, of rats from each of the following groups: the normal group (Control), the treatment group (DMN+ZC008 W, wherein "ZC008 W" refers to the aqueous *Graptopetalum* extract), the positive control group (DMN+Silymarin), and the negative control group (DMN).

FIG. 4 shows the microscopic photographs of liver tissues, stained with Sirius Red and Fast Green, of rats from each of the following groups: the normal group (Control), the treatment group (DMN+ZC008 W, wherein "ZC008 W" refers to the aqueous *Graptopetalum* extract), the positive control group (DMN+Silymarin), and the negative control group (DMN).

FIG. 5 shows the cytotoxic effect of the aqueous *Graptopetalum* extract on hepatic stellate cells (HSCs): (A) a diagram showing the dose- and time-dependent cycotoxic effect; (B) microscopic photographs of normal HSCs (Control) and HSCs treated with 1 mg/ml of the aqueous *Graptopetalum* extract (ZC008) after 5 days of culture.

FIG. 6 shows the regulatory effect of the aqueous *Graptopetalum* extract on immunological molecules: (A) a diagram showing its dosage-dependent inhibitory effect on TNF-α release; (B) a diagram showing its dosage-dependent inhibitory effect on IL-6 release; (C) a diagram showing its dosage-dependent promotional effect on IL-10 release.

FIG. 7 shows the protective effect of the aqueous *Graptopetalum* extract on hepatocytes: (A) a diagram showing its promotional effect on hepatocyte proliferation; (B) a diagram showing its protective effect on hepatocytes damaged by 1 mg/ml of acetaminophen.

DETAILED DESCRIPTION OF THE INVENTION

Figure 1:
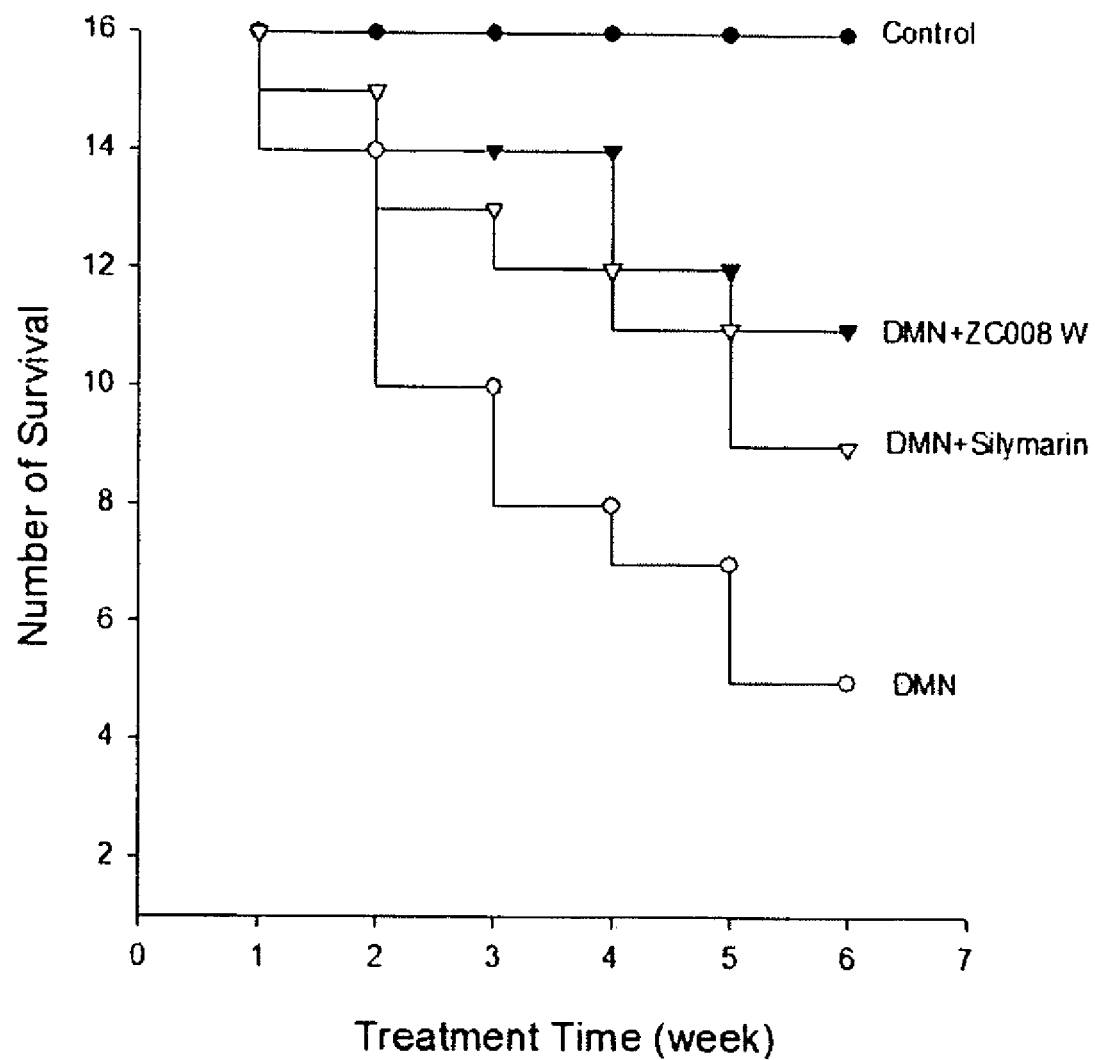

The present invention is directed to compositions comprising a water-soluble fraction of *Graptopetalum*, and uses thereof. *Graptopetalum* can protect animals from a toxic substance that causes inflammation and fibrosis of the liver, weight loss, spleen swelling, and ultimately death. In particular, *Graptopetalum* inhibits proliferation of activated hepatic stellate cells, which play a pivotal role in liver fibrosis. Therefore, *Graptopetalum* is a prophylactic and therapeutic agent, particularly for liver-related diseases and medical conditions.

Prior to describing the invention in further detail, the terms used in this application are defined as follows unless otherwise indicated.

DEFINITIONS

"*Graptopetalum*", as used herein, refers to any plant in the genus of *Graptopetalum*, or part or parts thereof. The plant parts may include, without being limited to, leaves, flowers, stalks, roots, fruits, and seeds. This term also encompasses modified forms of the plant or part(s), such as powders, extracts, dried extracts, homogenates, granules, or precipitates. Combinations of more than one species of *Graptopetalum*, or parts thereof, are also contemplated. The *Graptopetalum* used in the present invention is preferably *G. paraguayense*.

The term "water-soluble fraction of *Graptopetalum*" used herein refers to any fraction from *Graptopetalum* that is capable of being substantially dissolved in water. A water-soluble fraction of *Graptopetalum* can be prepared by extracting *Graptopetalum* with water or an aqueous solution to obtain an aqueous *Graptopetalum* extract via any standard method commonly known in the art.

An "extract" is a solution obtained by soaking or mixing a substance to be extracted with a solvent. A *Graptopetalum* extract can be prepared as follows. A whole *Graptopetalum* plant is dried and then subjected to cutting or grinding to form *Graptopetalum* powder. The powder is extracted with a suitable solvent, such as water, ethanol, ethanol/water mixture, methanol, propanol, iso-propanol, butanol, iso-butanol, acetone, hexane, petroleum ether, or other suitable organic solvents, by means of, e.g., maceration, percolation, repercolation, counter-current extraction, turbo-extraction, or carbon-dioxide hypercritical (temperature/pressure) extraction. The extract thus obtained can be concentrated by, e.g., evaporation, to produce a semi-dry extract (extractum spissum) or a dry extract (extracum siccum) by, e.g., spray drying, vacuum drying, fluid-bed drying, or freeze-drying. Preferably, the extract is prepared without boiling *Graptopetalum*. It is also preferable that no oil is used to extract the plants.

The term "liver disease or medical condition" used herein refers to a disease or medical condition involved with damages of the liver, or any part thereof. Liver diseases and medical conditions include, without being limited to, liver fibrosis, liver cirrhosis, chronic hepatitis (such as A, B, C, D, E, or other forms), non-alcoholic fatty liver, alcoholic fatty liver, and liver tumors (particularly hepatic carcinoma). Preferably, the disease or medical condition is selected from the group consisting of liver inflammation, liver steatosis, liver fibrosis, liver cirrhosis, and hepatitis. Examples of "hepatitis" include hepatitis A, hepatitis B, hepatitis C, hepatitis D, and hepatitis E. The term "liver steatosis" used herein refers the accumulation of fat globules within the cells of the liver, resulting in deterioration of tissue and diminished functioning of the liver. It can be induced by certain drugs or chemical compounds (e.g., tetracyclines, cortisone, phosphorous and carbon tetrachloride), nutritional causes (e.g., starvation and obesity), or endocrine causes (e.g, diabetes mellitus and fatty liver of pregnancy).

"Preventing" a disease or medical condition means preventing the symptoms of the disease or medical condition from manifestation prior to onset of the disease or medical condition.

The term "treating" is defined as administration of a composition to a subject with the purpose to cure, alleviate, relieve, remedy, prevent, or ameliorate a disorder, a symptom of the disorder, a disease state secondary to the disorder, or a predisposition toward the disorder.

An "effective amount" is an amount of a composition that is capable of producing a medically desirable result as described above in a treated subject. For example, an effective amount of the water-soluble fraction of *Graptopetalum* for treating liver cirrhosis is an amount sufficient to reduce or ameliorate the symptoms of liver cirrhosis, as compared to the symptoms manifested in the absence of the *Graptopetalum* fraction. The effective amount of a given agent will vary with factors such as the nature of the agent, the route of administration, the size and species of the animal to receive the agent, and the purpose of the administration. The effective amount in each individual case may be determined empirically by a skilled artisan according to the disclosure herein and established methods known in the art.

The term "unit dosage forms" refers to physically discrete units suitable as unitary dosages for human subjects and other mammals, each unit containing a predetermined quantity of *Graptopetalum* calculated to produce the desired effect, in association with a suitable pharmaceutical excipient.

*Graptopetalum* is a succulent plant with leaves arranged in the shape of rosettes. The genus *Graptopetalum* contains 12 species, including *G. paraguayense* (Ghost Plant), *G. amethystinum* (Lavender Pebbles), *G. bellum* (also known as *Tacitus bellus*), and *G. macdougallii*.

According to the invention, the water-soluble fraction of *Graptopetalum* can be prepared by any standard method or technology commonly known in the art. In one embodiment of the present invention, the water-soluble fraction of *Graptopetalum* is an aqueous *Graptopetalum* extract prepared by freeze drying whole plants of *Graptopetalum* and subsequently grinding the dried plants to powder, which is subjected to lyophilization. The powder is then extracted with water to obtain a pink aqueous extract, which may be lyophilized for easy storage and application.

In order to examine the effects of *Graptopetalum* on damaged liver, an animal model of liver injuries was used. Rats were injected with a toxic chemical, dimethylnitrosamine (DMN), which caused inflammation and fibrosis in the liver. Liver functions were lower in these animals, as indicated by a variety of biochemical parameters. Body weight and liver weight both declined, while spleen weight increased, and the majority of these animals died within weeks. In contrast, the rats that received a water-soluble fraction of Graptopetalum in addition to DMN had nearly normal body and liver weights, and their spleens did not swell (Examples 1 and 2). The majority of these animals survived, and their serum liver function indicators, including aspartate aminotransferase (AST), alanine aminotransferase (ALT), bilirubin, albumin, triglyceride (TG), cholesterol, and platelet, were of relatively normal levels (Example 3). In one example of the invention, the aqueous *Graptopetalum* extract dramatically reduced the damaging effects of DMN on the liver. A known therapeutic agent for the liver, silymarin (Saller R. et al., 2001, *Drugs* 61(14): 2035-2063), was examined in parallel as a positive control. Silymarin was also capable of increasing animal survival, body and liver weights, as well as liver functions. The water-soluble fraction of *Graptopetalum* (i.e. the aqueous *Graptopetalum* extract), however, was even more effective than silymarin.

The effects of *Graptopetalum* on liver fibrosis were also examined. After DMN treatment, a fine, uniform granulation was observed on the surface of the liver. Microscopic analysis revealed cirrhotic-like structural patterns in the liver: fibrous connective tissue formed by Glisson's sheath and pseudolobule, fibrotic septa formed by fibrous connective tissue, and reticulin fibers extending outward from the center. Animals treated with both DMN and silymarin still exhibited intense centrilobular and periportal deposition of fibrous connective tissues. In contrast, the livers of DMN-treated rats that received the water-soluble fraction of *Graptopetalum* (i.e. the aqueous *Graptopetalum* extract) showed only mild bridging fibrosis, diminished fibrosis in both the periportal and centrilobular areas, and reduced deformation of hepatic lobules (Example 5).

In a fibrotic liver, extracellular matrix accumulates. The increased levels of extracellular matrix are crucial for further progression of fibrosis, which ultimately leads to liver cirrhosis. Since collagen is a main component in the extracellular matrix, we determined the collagen content of animals treated with DMN alone or the combination of DMN and the water-soluble fraction of *Graptopetalum* (i.e. the aqueous *Graptopetalum* extract). Although there were very low levels of collagen deposition in the livers of control rats, DMN-treated rats displayed bundles of collagen surrounding the lobules and large fibrous septa, indicating the onset of severe fibrosis (Example 6).

The hepatic stellate cells (HSCs) are responsible for the increase in extracellular matrix in the fibrotic liver. Upon activation, HSCs undergo cell proliferation and increased fibrogenesis to result in fibrosis (see, e.g., Friedman S. L., 1993, *N Engl J Med*. 328(25): 1828-1835). We incubated cultured HSCs with the water-soluble fraction of *Graptopetalum* (i.e. the aqueous *Graptopetalum* extract) to determine the possible mechanism of *Graptopetalum* action on HSCs. The results showed that the water-soluble fraction of *Graptopetalum* (i.e. the aqueous *Graptopetalum* extract) inhibited HSC proliferation in a time- and dosage-dependent manner. After overnight incubation, the HSCs changed in morphology, detached from the culture container, and died (Example 7). In contrast, hepatocytes, which were incubated in the same fashion, were not significantly affected (Example 9). Thus, *Graptopetalum* is selectively cytotoxic to HSCs.

We have also examined the effect of *Graptopetalum* on several immunological molecules to further assess the potential of *Graptopetalum* for treating liver inflammation. Kupffer cells are specialized macrophages located in the liver that form part of the reticuloendothelial system (i.e., the mononuclear phagocyte system). Cultured Kupffer cells were induced for inflammatory reactions, and then incubated with the water-soluble fraction of *Graptopetalum* (i.e. the aqueous *Graptopetalum* extract). The results showed that the release of immunological molecules by the cells were regulated by *Graptopetalum* in a pattern in favor of inhibiting the inflammatory reactions (Example 8).

Accordingly, the present invention provides a method of preventing or treating a liver disease or medical condition in a subject, comprising administering an effective amount of a water-soluble fraction of Graptopetalum to the subject, wherein the liver disease or medical condition is selected from the group consisting of liver inflammation, liver steatosis, liver fibrosis, liver cirrhosis, and hepatitis B.

The amount of water-soluble fraction of *Graptopetalum* (or the aqueous *Graptopetalum* extract) is preferably sufficient to reduce collagen formation and/or to inhibit HSC proliferation in the liver of the subject. The subject may begin to receive water-soluble fraction of *Graptopetalum* before any sign of liver fibrosis is manifest; alternatively, the subject may receive water-soluble fraction of *Graptopetalum* after liver fibrosis, or even cirrhosis, has begun. Almost all chronic liver conditions eventually cause liver cirrhosis. Therefore, the water-soluble fraction of *Graptopetalum* can be used to ameliorate the symptoms of a variety of liver diseases or conditions, including chronic hepatitis (such as A, B, C, D, E, or other forms), non-alcoholic fatty liver, alcoholic fatty liver, and liver tumors (particularly hepatic carcinoma).

In an embodiment of the present invention, there is provided a method of inhibiting HSC proliferation by using a water-soluble fraction of *Graptopetalum* (i.e. an aqueous *Graptopetalum* extract). HSC proliferation may be measured by counting HSC numbers, determining biochemical markers of HSC (such as α-SMA mRNA or protein expression), determining collagen levels, or any other methods established in the art.

In another embodiment of the present invention, there is provided a method for preventing or treating inflammation in the liver of a subject, comprising administering an effective amount of a water-soluble fraction of Graptopetalumto the subject. It is contemplated that *Graptopetalum* can be used alone or in conjunction with other anti-inflammatory agents. These other anti-inflammatory agents may include, without being limited to, glucocorticoids, aspirin, ibuprofen, cyclopentenone prostaglandins, sesquiterpene lactones, sulfasalazine, chlorpheniramine maleate, clemastine, and deoxyspergualin. When the water-soluble fraction of *Graptopetalum* is administered in combination with at least one other anti-inflammatory agent, the water-soluble fraction of *Graptopetalum* and the other agent may be mixed in one composition for administration to the subject, or they can be administered separately.

In yet another embodiment of the present invention, there is provided a method for treating or preventing hepatitis B virus infection in a subject, comprising administering to the subject an effective amount of an water-soluble fraction of *Graptopetalum*. The water-soluble fraction of *Graptopetalum* can be used alone or in conjunction with other anti-viral agents. These other anti-viral agents may include, without being limited to, interferon, lamivudine (3TC), adefovir, ribavirin, specific antibodies for the virus of interest, and combinations thereof. When the water-soluble fraction of *Graptopetalum* is administered in combination with at least one other anti-viral agent, the water-soluble fraction of *Graptopetalum* and the other agent may be mixed in one composition for administration to the subject, or they can be administered separately.

The subject that receives a water-soluble fraction of *Graptopetalum* according to the present invention is preferably a mammal, more preferably a mammal selected from the group consisting of human, non-human primate, feline, canine, murine, rodent, equine, porcine, bovine and ovine, and most preferably a human. Preferably, the subject either suffers from a liver disease or medical condition, or is at risk for a liver disease or medical condition. A subject is at risk for a liver disease or medical condition if, for example, the subject consumes an above-normal level of alcohol frequently, has a family history of chronic liver diseases or conditions, expects to need blood transfusions, or is easily exposed to any hepatitis virus or hazardous material.

*Graptopetalum* does not have detectable side effects. As shown in Examples 7 and 9, *Graptopetalum* is selectively cytotoxic to HSCs, and even exerts a protective effect on normal hepatocytes. Therefore, it is of particular interest for a subject to use the water-soluble fraction of *Graptopetalum* as a health/nutrition food on a regular basis. Thus, the water-soluble fraction of *Graptopetalum* can be mixed in food or feed, made into a drink, taken in the form of tablets, capsules, pills, powders, or the like. For the ease of regular consumption, packets comprising powders of the a water-soluble fraction of *Graptopetalum* can be prepared that can be easily made into a drink. Cookies, crackers, cakes, chips, or other snacks that contain the water-soluble fraction of *Graptopetalum* are also contemplated. In general, the recommended daily dosage of the water-soluble fraction of *Graptopetalum* is the equivalent of from 0.1 grams to 30 grams of the *Graptopetalum* whole plant (wet weight) per kilogram body weight. The dosage is preferably 0.3 to 20, more preferably 0.5 to 15, and yet more preferably 1 to 10 (grams per kilogram body weight).

Although the preferred route of administration is oral, the water-soluble fraction of *Graptopetalum* can be administered in any other manner. For example, it can be administered subcutaneously, intravascularly, intravenously, intraperitoneally, topically, nasally, or pulmonarily.

This invention also includes pharmaceutical compositions which contain, as the active ingredient, an water-soluble fraction of *Graptopetalum*, as well as pharmaceutically acceptable carriers or excipients.

In making the compositions of this invention, the water-soluble fraction of *Graptopetalum* is usually mixed with an excipient, diluted by an excipient, or enclosed within such a carrier which can be in the form of a capsule, sachet, paper, or other container. When the pharmaceutically acceptable excipient serves as a diluent, it can be a solid, semi-solid, or liquid material, which acts as a vehicle, carrier, or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills, and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, acetyl alcohol, and cellulose acetate.

The liquid forms in which the compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device, or the nebulizing device may be attached to a face mask tent, or intermittent positive pressure breathing machine. Solution, suspension, or powder compositions may be administered, preferably orally or nasally, from devices which deliver the formulation in an appropriate manner.

Another preferred formulation employed in the methods of the present invention employs transdermal delivery devices ("patches"). Such transdermal patches may be used to provide continuous or discontinuous infusion of *Graptopetalum* in controlled amounts. The construction and use of transdermal patches for the delivery of pharmaceutical agents is well known in the art. See, for example, U.S. Pat. No. 5,023,252, herein incorporated by reference. Such patches may be constructed for continuous, pulsatile, or on-demand delivery of pharmaceutical agents.

Other suitable formulations for use in the present invention can be found in Remington's Pharmaceutical Sciences.

The pharmaceutical composition may be provided in convenient kits wherein the necessary materials are packaged into suitable containers. The compositions can be administered in a single dose, or multiple doses (i.e., more than one dose). The multiple doses can be administered concurrently, or consecutively (e.g., over a period of days or weeks). The compositions are preferably formulated in a unit dosage form, each dosage containing the equivalent amount of from about 1 to 500 grams of the whole *Graptopetalum* plant (wet weight).

It is further contemplated that the compositions of the present invention may be administered in conjunction with a known anti-inflammatory agent, anti-steatosis agent, anti-viral, or anti-fibrosis agent. In addition, other substances commonly used to protect the liver, such as silymarin, can also be used in conjunction with the *Graptopetalum* composition. All of these agents or substances can be mixed in the same composition with the water-soluble fraction of *Graptopetalum*, or administered separately.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

EXAMPLES

In the examples below, the following abbreviations have the following meanings: BW=body weight; ° C.=degree Celsius; hr=hour; min=minute; sec=second; M=molar; mM=millimolar; μM=micromolar; L or l=liter; ml=milliliter; μl=microliter; G or g=gram; mg=milligram; μg=microgram; DMEM=Dulbecco's modified Eagle's medium; DMN=dimethylnitrosamine; FBS=fetal bovine serum; GSSG=glutathione disulfide; HRP=horse radish peroxidase; LPS=lipopolysaccharide; NADPH=nicotinamide adenine dinucleotide phosphate; and PBS=phosphate buffered saline. Abbreviations not defined have their generally accepted meanings.

Preparation of an Aqueous *Graptopetalum* Extract

*Graptopetalum* was purchased from a local herb farm in Taiwan. Whole plants of *Graptopetalum* were washed with distilled water and air dried overnight, then freeze dried at −50° C. with a freeze dryer. *Graptopetalum* was then ground to powder (100 mesh), lyophilized, and stored under sealing condition at 4° C. until use. To prepare an aqueous extract, 5 grams of the *Graptopetalum* powder prepared by the method described above were extracted two times, each by suspending in 250 ml of water at 25° C. for 2 hours on a rotary shaker at 100 rpm. The two resultant water extracts were combined. As an example of the water-soluble fraction of *Graptopetalum*, an aqueous *Graptopetalum* extract was obtained, as being pink in color after lyophilization.

Animals

Male Sprague-Dawley rats were purchased from the National Laboratory Animal Breeding and Research Center, National Science Council, Taiwan. The animals were 8-week old and weighed about 250 g at the start of the experiments. They were housed in a room with controlled temperature (21° C.) and humidity (60±10%) under a 12:12 h light-dark cycle. They were allowed free access to food and water. All experiments were performed in compliance with The National Laboratory Animal Breeding and Research Center's guidelines.

Administration of Test Material

The rats were divided randomly into four experimental groups (n=16 in each group) as follows:

(1) Normal group: injection of PBS i.p. and oral administration of water;

(2) Negative control group: injection of DMN i.p. and oral administration of water;

(3) Positive control group: injection of DMN i.p. and oral administration of silymarin; and (4) Treatment group: injection of DMN i.p. and oral administration of the aqueous *Graptopetalum* extract.

Liver injury and fibrosis model rats were prepared by administration of DMN as previously reported by Jezequel et al. (Jezequel A. M. et al., 1997, *J. Hepatol.* 5: 174-181). Briefly, DMN (Sigma Company, St. Louis, Mo.) was diluted with PBS and injected intraperitoneally (i.p.) into rats on the first three days of each week, at the dosage of 5 mg/kg BW per day, for the first three weeks of the experiment period. The normal group received injection of PBS alone.

Aqueous *Graptopetalum* extract (lyophilisate) and silymarin (Sigma Company, St. Louis, Mo.) were dissolved in 10 ml of water and given orally once per day at a dosage of 0.4 mg/kg BW and 200 mg/kg BW, respectively, everyday from the second week during the whole experiment period of 6 weeks. Animals of the other two groups received the same volume of distilled water alone. All rats were weighed every week and their body weights were recorded. Blood samples were collected from their tails in the first and third weeks for determination of biochemical indicators. After the six-week experiment period, the rats were sacrificed, blood samples were collected from the abdominal aorta for determination of biochemical indicators, and livers and spleens were excised, weighed, and fixed in formalin for histochemistry.

Statistical Analysis

The data obtained in the experiments were analyzed by ANOVA (analysis of variance) with the SPSS computer statistical software. A value of P<0.05 was considered to be statistically significant.

Effects of an Aqueous *Graptopetalum* Extract on the Changes of Body, Liver and Spleen Weights Induced by DMN To determine the effects of the aqueous *Graptopetalum* extract on liver injury and fibrosis, an animal model was established using DMN, a known toxic substance to the liver. Animals which received DMN, as described above, were then given the aqueous *Graptopetalum* extract and the effects determined. The effects of the aqueous *Graptopetalum* extract were also compared to those of silymarin, which has known hepatoprotective activities. Normal animals, which did not receive DMN, were used as controls.

The data obtained are shown in the following tables. Table 1 contains the body, liver and spleen weights, as well as the survival number of each group of rats at the end of the experiment. Table 2 contains the survival number and body weight of each group of rats at the end of the first and third weeks. As can be seen from these data, treatment with DMN caused a significant decrease in the body and liver weights, but an increase in the spleen weight of the rats of the negative control group, as compared with those of the rats of the normal group. Oral administration of the aqueous *Graptopetalum* extract not only markedly prevented this DMN-resulted rat body and liver weight loss, but also reduced the DMN-induced rat spleen swelling (treatment group). These results indicate that the aqueous *Graptopetalum* extract of the present invention significantly reduced the detrimental impacts of DMN.

TABLE 1

Body, Liver, and Spleen Weights and Survival Number after 6 Weeks of Treatment

|  | Survival Number | Body Weight (g) | Liver Weight (g) | Spleen Weight (g) |
| --- | --- | --- | --- | --- |
| Normal | 16 | 555.0 ± 28.3 | 24.8 ± 3.1 | 1.0 ± 0.0 |
| DMN + d.d.H$_2$O | 5 | 344.6 ± 10.3** | 11.8 ± 1.4** | 2.4 ± 0.3** |
| DMN + *Graptopetalum* | 11 | 375.1 ± 15.3** | 16.5 ± 7.4** | 1.5 ± 0.3** |
| DMN + Silymarin | 9 | 361.3 ± 6.1** | 17.9 ± 2.0** | 1.6 ± 0.1** |

*p < 0.05;
**p < 0.01 (compared with Normal).

TABLE 2

Body Weight and Survival Number after 1 and 3 Weeks of Treatment

|  | 1 Week | | 3 Weeks | |
| --- | --- | --- | --- | --- |
|  | Survival Number | Body Weight (g) | Survival Number | Body Weight (g) |
| Normal | 16 | 430.6 ± 9.6 | 16 | 434.8 ± 12.2 |
| DMN + d.d.H$_2$O | 16 | 431.7 ± 10.7 | 10 | 344.6 ± 10.3** |
| DMN + *Graptopetalum* | 16 | 448.8 ± 21.9 | 14 | 375.1 ± 15.3** |
| DMN + Silymarin | 16 | 442.1 ± 18.9 | 13 | 361.3 ± 6.1** |

*p < 0.05;
**p < 0.01 (compared with Normal).

Protection Effects of an Aqueous *Graptopetalum* Extract on DMN-Treated Rats

As shown in FIG. 1, at the end of the 6-week experiment, no rats in the normal group died, but 11 rats in the negative control group died. As for the rats treated with the aqueous *Graptopetalum* extract, only 5 out of 16 died, while in the silymarin-treated group (positive control) 7 out of 16 rats died.

Figure 2:
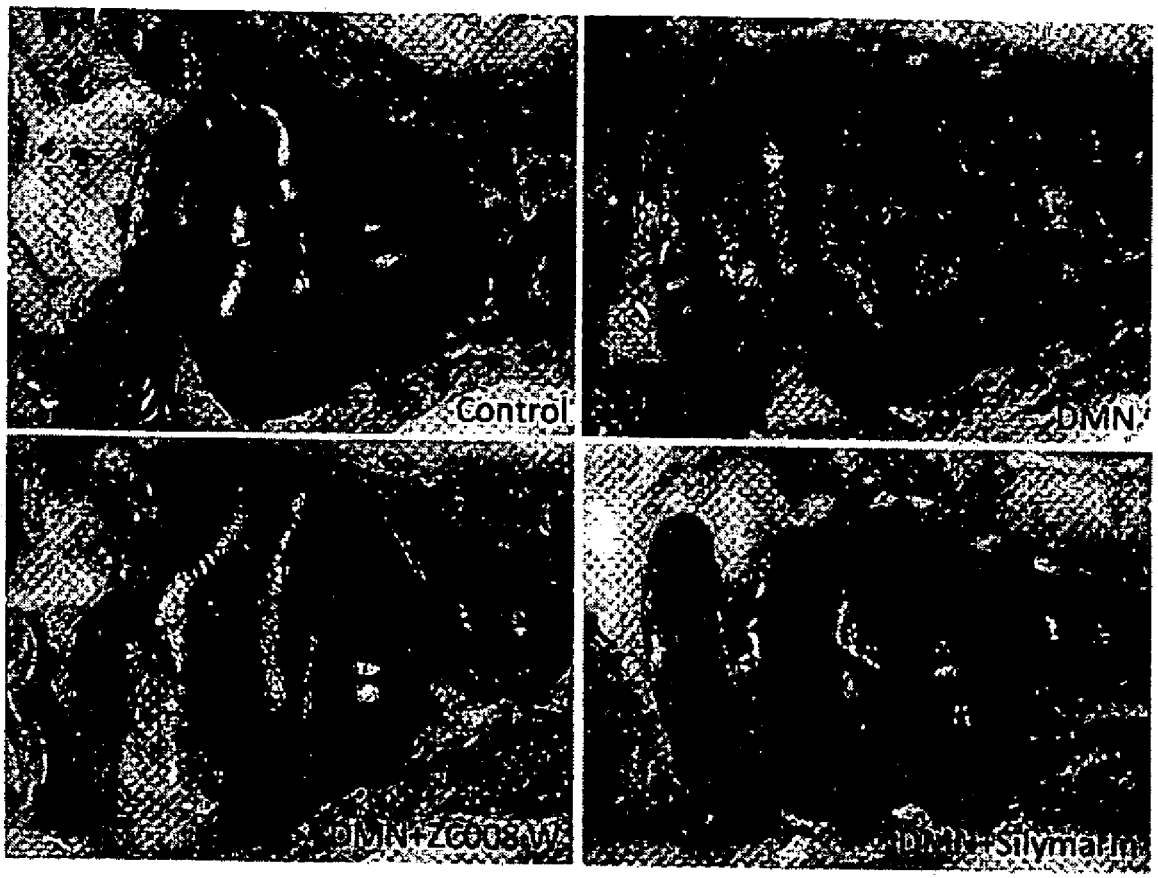

In addition, as can be seen from the photos shown in FIG. 2, all the groups treated with DMN exhibited coarse and swelling livers and spleens, except for the group receiving the aqueous *Graptopetalum* extract. Such results indicate that the aqueous *Graptopetalum* extract of the present invention indeed reduced the damage caused by DMN.

Effects of an Aqueous *Graptopetalum* Extract on Serum Biochemical Indicators for Liver Functions To further investigate the effects of the aqueous *Graptopetalum* extract on liver functions, indicators of liver functions were measured. All the blood samples were left under room temperature for 1 hr for coagulation, and then centrifuged with a refrigerated centrifugator under 4° C. at a speed of 12,000 rpm/min for 5 mins to separate the serum (Lin, J. M. et al., 1997, *Am. J. Chin. Med.* 21: 59-69). The biochemical indicators for liver functions, including aspartate aminotransferase (AST), alanine aminotransferase (ALT), bilirubin, albumin, triglyceride (TG), cholesterol, platelet and prothrombin time (PT), were determined by an automated biochemical analyzer commonly used in a hospital.

The data obtained are shown in the following tables. As can be seen from Tables 3, 4 and 5, treatment with DMN has raised serum AST, ALT and bilirubin levels. However, oral administration of the aqueous *Graptopetalum* extract not only lowered serum AST, ALT and bilirubin levels raised by the DMN treatment, but also increased serum albumin level. In addition, treatment with DMN has decreased the amount of platelet and increased PT, but oral administration of the aqueous *Graptopetalum* extract increased the amount of platelet and decreased PT (see Table 6). Accordingly, the aqueous *Graptopetalum* extract of the present invention significantly enhanced liver functions.

TABLE 3

Serum Levels of AST, ALT, Bilirubin, Albumin, TG and Cholesterol after 1 Week of Treatment

|  | AST (U/L) | ALT (U/L) | Bilirubin (μmole/L) | Albumin (g %) | TG (mg/dl) | Cholesterol (mg/dl) |
|---|---|---|---|---|---|---|
| Control (n = 16) | 107.0 ± 7.0 | 84.6 ± 16.9 | 0.1 ± 0.0 | 4.7 ± 0.1 | 158.8 ± 5.6 | 128.2 ± 5.2 |
| DMN + d.d.H$_2$O (n = 16) | 110.8 ± 4.1 | 88.7 ± 14.5 | 0.1 ± 0.0 | 4.7 ± 0.1 | 163.6 ± 7.4 | 132.1 ± 7.8 |
| DMN + *Graptopetalum* (n = 16) | 112.1 ± 7.0 | 83.4 ± 13.8 | 0.1 ± 0.0 | 4.7 ± 0.1 | 164.6 ± 6.0 | 128.1 ± 6.5 |
| DMN + Silymarin (n = 16) | 111.7 ± 6.4 | 84.1 ± 14.4 | 0.1 ± 0.0 | 4.7 ± 0.1 | 164.8 ± 5.4 | 130.8 ± 7.0 | n, survival number.

TABLE 4

Serum Levels of AST, ALT, Bilirubin, Albumin, TG and Cholesterol after 3 Weeks of Treatment

|  | AST (U/L) | ALT (U/L) | Bilirubin (μmole/L) | Albumin (g %) | Triglyceride (mg/dl) | Cholesterol (mg/dl) |
|---|---|---|---|---|---|---|
| Control (n = 16) | 110.6 ± 29.6 | 82.4 ± 12.1 | 0.1 ± 0.0 | 4.8 ± 0.3 | 179.9 ± 24.0 | 88.1 ± 11.9 |
| DMN + d.d.H$_2$O (n = 10) | 579.6 ± 88.2** | 272.4 ± 12.6** | 0.5 ± 0.1** | 2.9 ± 0.3** | 305.0 ± 48.6** | 117.7 ± 7.3** |
| DMN + *Graptopetalum* (n = 14) | 324.4 ± 71.4** | 194.1 ± 55.6** | 0.1 ± 0.1 | 3.9 ± 0.6** | 211.7 ± 42.2* | 126.8 ± 11.4** |
| DMN + Silymarin (n = 13) | 415.5 ± 39.7 | 245.3 ± 48.7 | 0.4 ± 0.1 | 3.5 ± 0.7 | 222.2 ± 28.0 | 125.2 ± 11.1 | n, survival number;
*p < 0.05;
**p < 0.01 (compared with Normal).

TABLE 5

Serum Levels of AST, ALT, Bilirubin, Albumin, TG and Cholesterol after 6 Weeks of Treatment

|  | AST (U/L) | ALT (U/L) | Bilirubin (μmole/L) | Albumin (g %) | Triglyceride (mg/dl) | Cholesterol (mg/dl) |
|---|---|---|---|---|---|---|
| Control (n = 16) | 127.6 ± 16.2 | 88.8 ± 7.4 | 0.1 ± 0.1 | 5.0 ± 0.3 | 218.9 ± 15.5 | 130.1 ± 9.1 |
| DMN + d.d.H2O (n = 5) | 818.2 ± 43.6** | 427.2 ± 44.8** | 0.7 ± 0.1** | 2.5 ± 0.4** | 475.8 ± 56.8** | 222.8 ± 105.4** |
| DMN + *Graptopetalum* (n = 11) | 314.9 ± 19.1** | 195.9 ± 12.3** | 0.3 ± 0.0** | 3.8 ± 0.4** | 209.5 ± 15.2 | 126.7 ± 20.5 |
| DMN + Silymarin (n = 9) | 659.1 ± 30.6 | 338.2 ± 15.1 | 0.5 ± 0.1 | 3.1 ± 0.2 | 218.0 ± 41.2 | 128.2 ± 50.8 | n, survival number;
*p < 0.05;
**p < 0.01 (compared with Normal).

TABLE 6

Serum Level of Platelet and PT after 6 Weeks of Treatment

|  | PT (sec) | Platelet (10$^3$/ul) |
|---|---|---|
| Control (n = 16) | 12.9 ± 0.5 | 1.0 ± 0.0 |
| DMN + d.d.H$_2$O (n = 5) | 16.3 ± 1.5** | 2.4 ± 0.3** |
| DMN + *Graptopetalum* (n = 11) | 13.2 ± 1.0 | 1.5 ± 0.3** |
| DMN + Silymarin (n = 9) | 15.0 ± 0.5 | 1.6 ± 0.1 | n, survival number;
*p < 0.05;
**p < 0.01 (compared with Normal).

Effects of an Aqueous *Graptopetalum* Extract on Antioxidant Molecules

After the rats were sacrificed at the end of the 6-week experiment, 5 tissue samples were obtained from their liver for determination of the concentration or enzymatic activity of the following antioxidant molecules: glutathione (GSH), glutathione peroxidase (GSH Px), glutathione reductase (GSH Rd), superoxide dismutase (SOD), and catalase (CAT).

The concentration of GSH was determined with the Glutathione Assay Kit (Cat. No. 354102) from Calbiochem-Merck (Cambridge, Mass.). The liver tissue sample was first homogenized, and Solution 3 was added to the homogenized sample until the sample volume reached 900 μl. Solution R1 (50 μl) and Solution R2 (50 μl) were then added to and thoroughly mixed with the sample. The mixture was incubated at 25±3° C. in the dark for 10 mins before the absorbance at 400 nm was determined by a spectrophotometer. The concentration of GSH was calculated with a multiple calibration curve, and expressed as μmol/g tissue.

The enzymatic activity of GSH Px was determined with the Glutathione Peroxidase, Cellular, Assay Kit (Cat. No. 354104) from Calbiochem-Merck (Cambridge, Mass.). A homogenized liver tissue sample was mixed with 0.8 ml of NADPH Reagent and incubated at 23 to 25° C. for 5 mins. Then, 0.1 ml of 2.5 mM t-butyl hydroperoxide was added to the mixture, and the absorbance at 340 nm was monitored for 3 mins so that the decreasing rate of NADPH could be calculated. The activity of GSH Px was calculated from the decreasing rate of NADPH and expressed as U/mg protein.

The enzymatic activity of GSH Rd was determined with the Glutathione Reductase Assay Kit (Cat. No. 359962) from Calbiochem-Merck (Cambridge, Mass.). A homogenized liver tissue sample was mixed with Assay Buffer at 25° C. Then, 0.9 ml of Sample Diluent Buffer (containing GSSG and NADPH) was added to the mixture, and the absorbance at 340 nm was monitored for 5 mins so that the decreasing rate of NADPH could be calculated. The activity of GSH Rd was calculated from the decreasing rate of NADPH and expressed as U/mg protein.

The enzymatic activity of SOD was determined with the Superoxide Dismutase Assay Kit (Cat. No. 574600) from Calbiochem-Merck (Cambridge, Mass.). Forty µl of homogenized liver tissue sample and 30 µl of Solution R2 were added into 900 µl of Buffer, and the resulted mixture was vortexed for mixing. The mixture was incubated at 37° C. for 1 min before 30 µl of Solution R1 was added and the mixture was vortexed again for mixing. The absorbance of the reaction mixture at 525 nm was monitored for 10 mins, and the change rate of the absorbance was calculated. The concentration of SOD was calculated with a multiple calibration curve, and the activity was expressed as U/mg protein.

The enzymatic activity of CAT was determined with the Catalase Assay Kit (Cat. No. 219263) from Calbiochem-Merck (Cambridge, Mass.). Thirty µl of homogenized liver tissue sample was added into 500 µl of Substrate (10 mM $H_2O_2$), and the mixture was incubated under room temperature for 1 min for reaction. After 1 min of reaction, 500 µl of Stop Reagent was added to stop the reaction. Twenty µl of the mixture was then added into 2 ml of HRP/Chromogen Reagent and allowed to react under room temperature for 10 mins, and the absorbance at 520 nm was measured. The concentration of CAT was calculated by an established formula, and the activity of CAT was expressed as U/mg protein.

The total protein concentration in the liver tissue was also determined as follows. A suitable amount of the liver tissue sample was taken, and its volume was adjusted to 100 µl with 1 N NaOH. To the sample 200 µl of deionized $H_2O$ and 100 µl of a reaction mixture (25% $Na_2CO_3$:2% Na—K-tratarate: 1% $CuSO_4$=8:1:1, v/v/v) were added, and the resulted mixture was incubated under room temperature for 10 mins. After 10 mins of reaction, 1 ml of Folin's Reagent was added to the mixture, and the resulted mixture was incubated in a 37° C. water bath for 20 mins. After the mixture was cooled down to 25° C. under room temperature, its absorbance at 660 nm was measured by a spectrophotometer. To calculate the protein concentration in the liver tissue sample, linear regression was applied to a standard curve to generate a formula, which is used to obtain the protein concentration.

Prevention of Hepatic Fibrogenesis by an Aqueous *Graptopetalum* Extract in DMN-Treated Rats After the rats were sacrificed at the end of the 6-week experiment, a liver specimen of 1×1 $cm^2$ was taken from the liver of the rats, and fixed with 10% phosphate-buffered formaldehyde. The fixed liver tissue was then embedded in paraffin and sectioned. The sections were stained with hematoxylin and eosin (reagents were obtained from Sigma Company, St. Louis, Mo.), and observed under a microscope (Olympus IX70, Japan).

Figure 3:
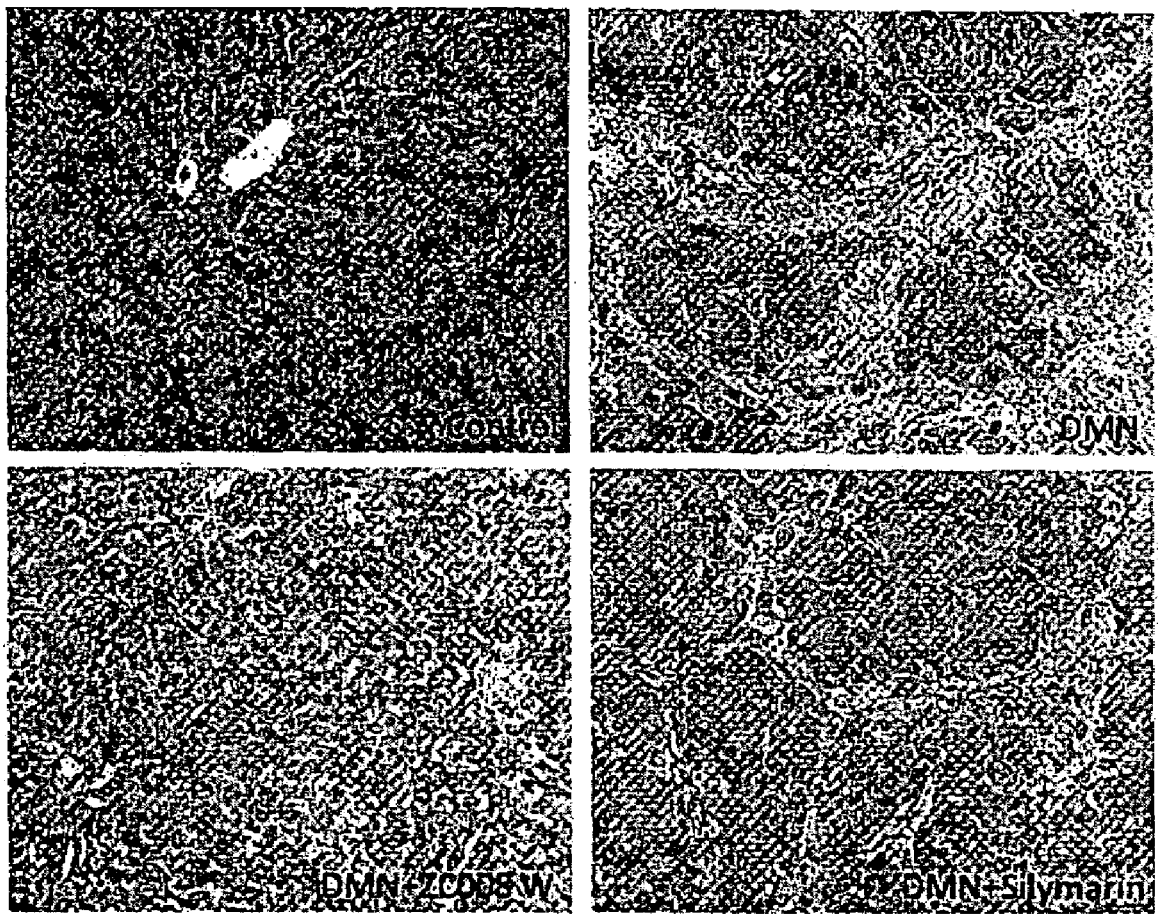

Intraperitoneal administration of DMN resulted in a coarse surface of the liver, and microscopic observation revealed that fibrogenesis has occurred in the liver tissue of the rats. As shown in FIG. 3, in the negative control group, Glisson's sheath and pseudolobule have formed fibrous connective tissue, which in turn formed fibrotic septa. In addition, reticulin fibers have extended outward from the center. In the positive control group which received silymarin, hepatic fibrogenesis is still clearly visible. In contrast, in the treatment group which received the aqueous *Graptopetalum* extract, hepatic fibrogenesis is mild and deformation of hepatic lobules is reduced. Thus, the aqueous *Graptopetalum* extract of the present invention effectively reduced the hepatic fibrogenesis resulted by DMN.

Reduction of Hepatic Collagen by an Aqueous *Graptopetalum* Extract in DMN-Treated Rats In a fibrotic liver, extracellular matrix accumulates. The increase of extracellular matrix is crucial for further progression of fibrosis, which ultimately leads to liver cirrhosis. Since collagen is a main component in the extracellular matrix, the change in collagen content of the rats was determined.

Liver tissue sections obtained as described in Example 5 were stained for collagen and observed under a microscope (Olympus IX70, Japan). Differential staining of collagenous and noncollagenous proteins was performed with 0.1% Sirius Red and 0.1% Fast Green as a counter staining in saturated picric acid (reagents were obtained from Curr, BDH Chemical, Canada). By this procedure collagen was stained red.

Figure 4:
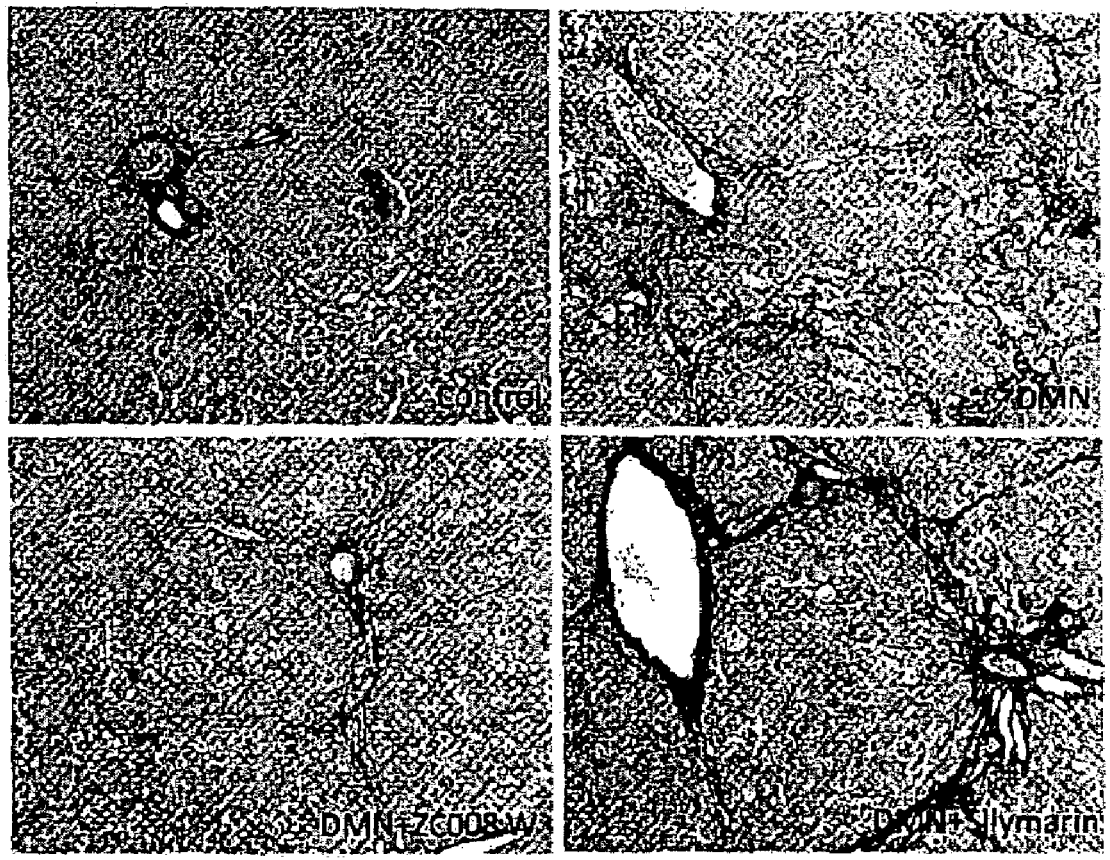

As shown in FIG. 4, in the negative control group collagen are widely distributed in the liver tissue. In addition, hepatic lobules are surrounded by a large amount of collagen fibers, indicating severe fibrosis. In the positive control group which received silymarin, collagen content is still high and hepatic lobules are still surrounded by collagen fibers. In contrast, merely a small amount of collagen presents in the treatment group which received the aqueous *Graptopetalum* extract. Consistent with the previous example, these results demonstrate that the aqueous *Graptopetalum* extract of the present invention markedly prevented hepatic fibrosis.

Cytotoxic Effect of an Aqueous *Graptopetalum* Extract on Hepatic Stellate Cells Specific liver cells, the hepatic stellate cells (HSCs), are responsible for the increase in extracellular matrix in the fibrotic liver. In normal livers, HSCs, which are lipocytes in nature, are the primary storage depot for retinoids. These cells can be identified by prominent intracellular droplets that contain vitamin A. Upon activation, HSCs undergo cell proliferation and increased fibrogenesis to result in fibrosis.

In this example, the effect of the aqueous *Graptopetalum* extract on HSCs was examined. To obtain HSCs, the livers of rats were digested with pronase and collagenase, and HSCs were isolated and cultured in DMEM containing 10% FBS. After 7 to 14 days of culture, the HSCs became activated into hepatic fiber-like cells and highly proliferated. The HSCs of the 4 to 30 generations were used for examination of the effect of the aqueous *Graptopetalum* extract.

Figure 5:
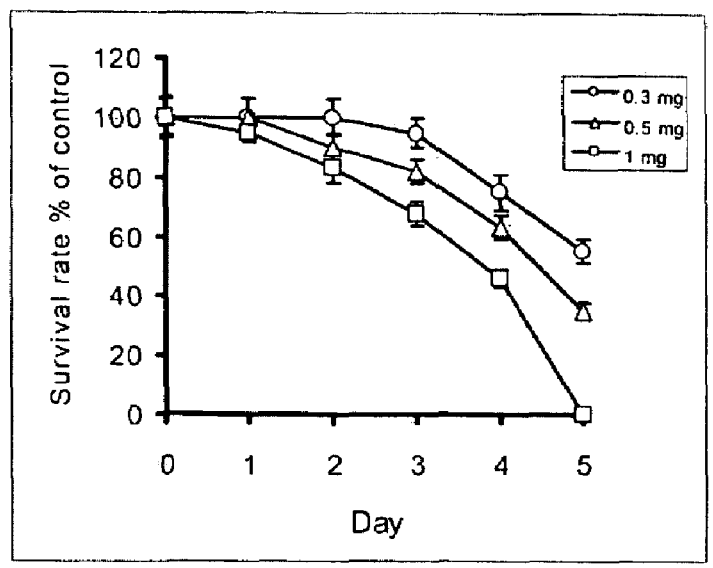
Figure 5:
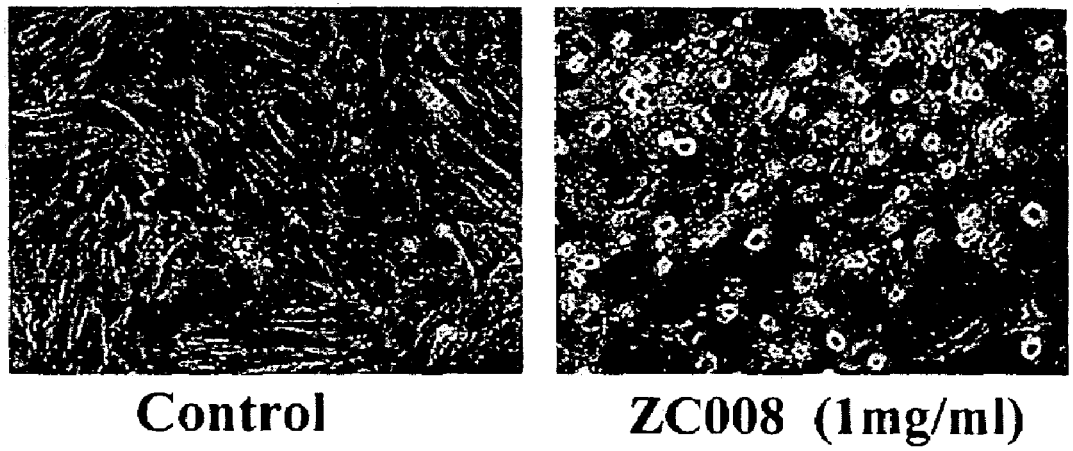

The HSCs, cultured at a density of $3 \times 10^4$ cells/well in a 12-well plate, were incubated overnight with 0.3, 0.5 or 1 mg/ml of the aqueous *Graptopetalum* extract under 37° C. and 5% $CO_2$. As can be seen from FIG. 5A, the aqueous *Graptopetalum* extract inhibited the cell growth of HSC in a dose- and time-dependent manner. In addition, the addition of a high dosage (1 mg/ml) of the aqueous *Graptopetalum* extract to the cultured activated rat HSCs resulted in striking morphologic alterations in HSCs after five days as observed under light microscopy. As can be seen from FIG. 5B, HSCs changed from a flattened fibroblastic phenotype with distinct cell-cell interfaces to a substratum-detached, rounded morphology, leaving a striking extracellular matrix net structure on the bottom of the culture flasks. Therefore, the aqueous

*Graptopetalum* extract of the present invention exhibited a cytotoxic effect on HSCs and ultimately resulted in cell death.

Regulatory Effects of an Aqueous *Graptopetalum* Extract on Immunological Molecules Kupffer cells are specialized macrophages located in the liver that form part of the reticuloendothelial system (i.e., the mononuclear phagocyte system). The primary function of Kupffer cells is to recycle old red blood cells that no longer are functional. To evaluate the effect of the aqueous *Graptopetalum* extract on liver inflammation, Kupffer cells isolated from rat livers were induced for inflammatory reactions, and the concentrations of secreted immunological molecules, including TNF-α, IL-6 and IL-10, were measured.

To obtain Kupffer cells, the livers of rats were digested with pronase and collagenase, and impurities in the digested sample were removed by centrifugation at 400×g. The cells were isolated by centrifugation on an iodixanol gradient of 11.7% to 14.7%. Isolated Kupffer cells were seeded in a 12-well plate and cultured with RPMI medium containing 10% FBS. After 2 hrs of culture, non-adherent cells were washed off so that the purity of the obtained Kupffer cells could reach 95% or higher. The cells were cultured for additional 48 hrs under 37° C. and 5% $CO_2$ before induction of inflammatory reactions.

Except for cells of the control group and LPS group, cells were treated with 0.3, 0.7 or 1 mg/ml of the aqueous *Graptopetalum* extract for 20 mins first. Then, 0.1 µg/ml of LPS was added to each group of cells except for the control group to induce inflammatory reactions. After 24 hours, supernatants were taken from the cultures and the concentrations of secreted TNF-α, IL-6 and IL-10 were determined by ELISA (as shown in FIG. 6).

Figure 6:
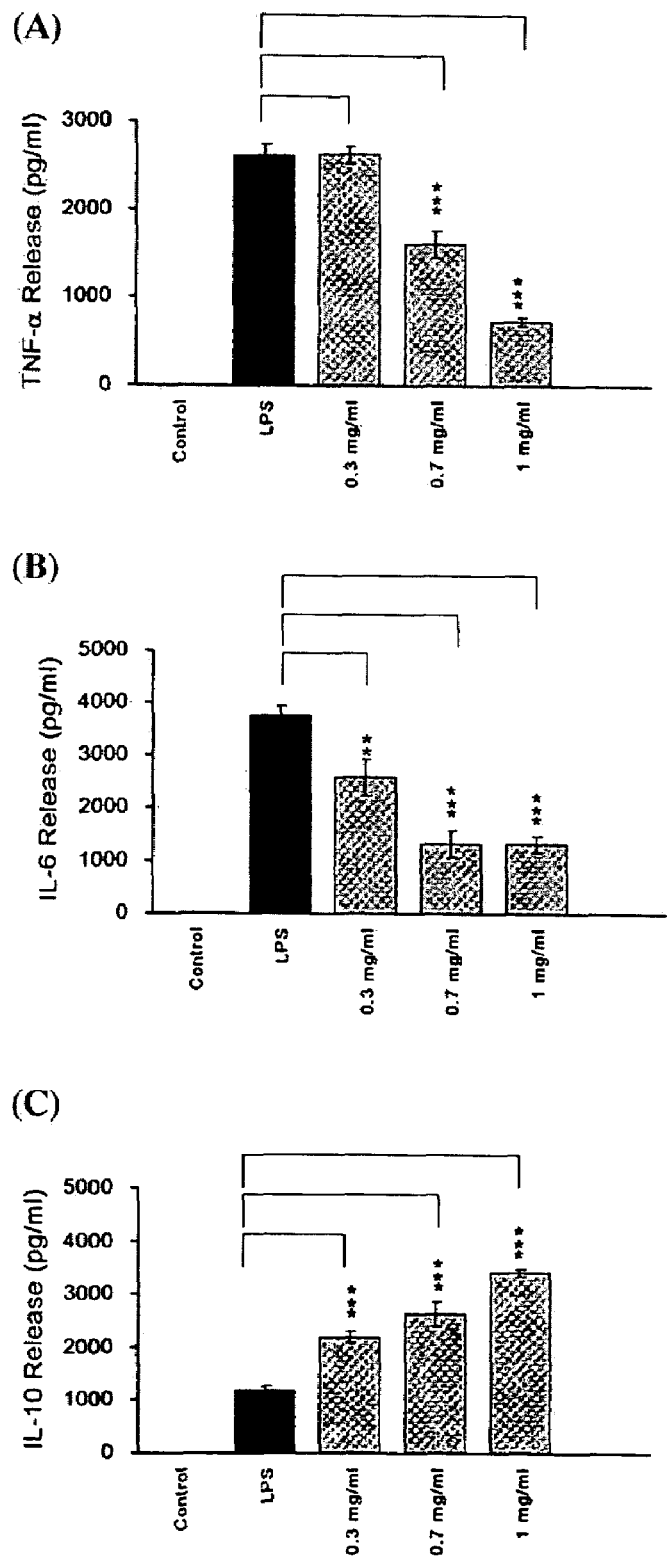

As shown in FIG. 6, the aqueous *Graptopetalum* extract inhibited the release of TNF-α and IL-6 but promoted the release of IL-10 in a dosage-dependent manner. These results indicate that the aqueous *Graptopetalum* extract of the present invention exhibited immuno-regulatory effects and has potential for inhibiting liver inflammation.

Protective Effect of an Aqueous *Graptopetalum* Extract on Hepatocytes

To evaluate if the aqueous *Graptopetalum* extract has a cytotoxic effect on hepatocytes, cultured rat hepatocytes were utilized in this example. Thoracotomy was applied to rats suffocated with $CO_2$, followed by profusion with 0.025% collagenase for 15 to 20 mins so that hepatocytes could amply dissociate. The membrane covering the liver was removed with pinchers and the liver tissue was cut into pieces with scissors. The cut-up liver tissue was left for further digestion for 45 mins, and cell suspension was collected every 5 mins. After filtration, the cell suspension was then centrifuged at 600 rpm (80×g) and the resulting supernatant was discarded. The cells were washed 3 times with L-15 solution before cultured in the hepatocyte culture medium (DMEM containing 2% FBS, $10^{-6}$ M dexomethane and 0.35 U/ml insulin).

Figure 7:
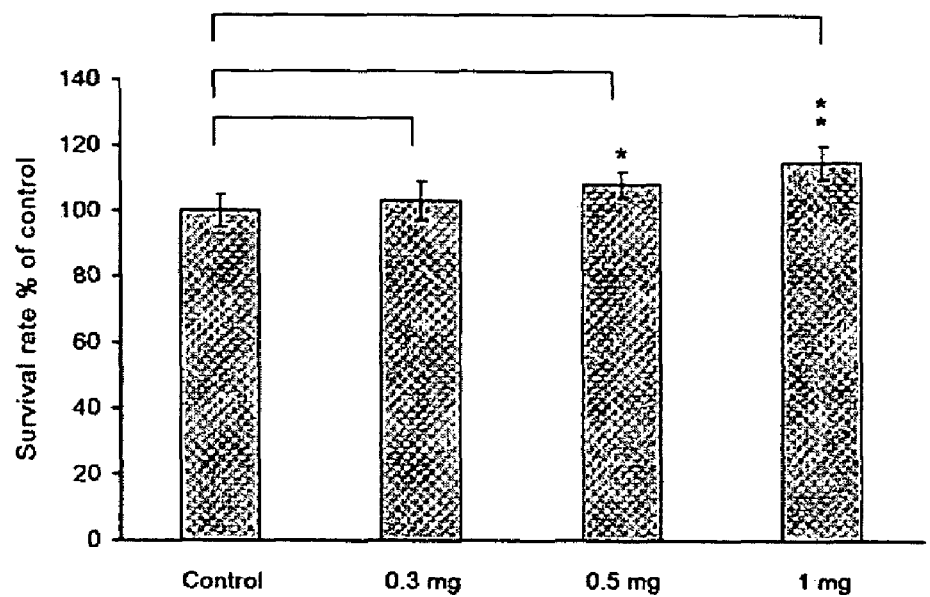
Figure 7:
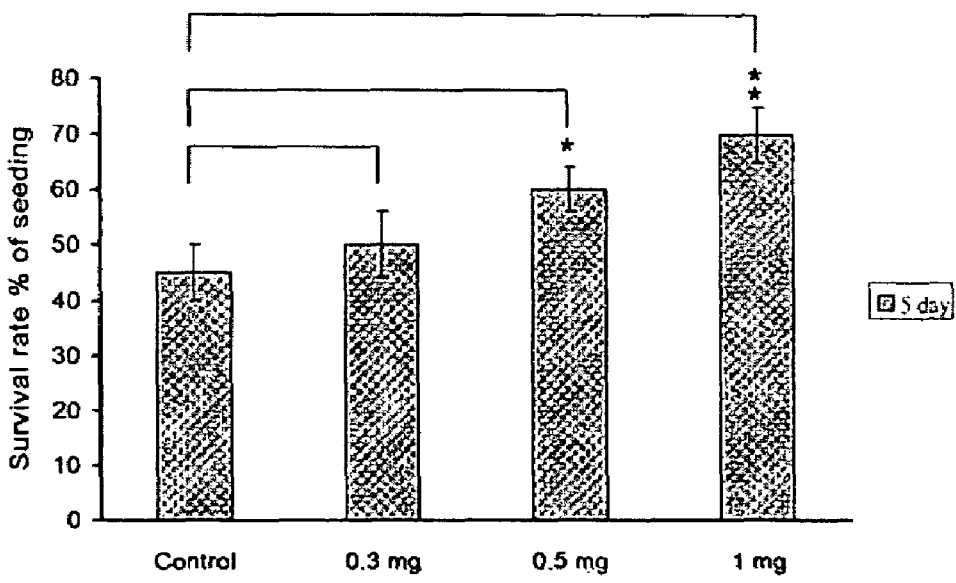

The hepatocytes, cultured at a density of $1×10^5$ cells/well in a 12-well plate, were incubated overnight with 0.3, 0.5 or 1 mg/ml of the aqueous *Graptopetalum* extract under 37° C. and 5% $CO_2$. The viability of the hepatocytes was determined by the MTT assay. As shown in FIG. 7A, the aqueous *Graptopetalum* extract enhanced cell proliferation in a dosage-dependent manner.

To further explore the protective effect of the aqueous *Graptopetalum* extract on hepatocytes, the hepatocytes were treated with 1 mg/ml of acetaminophen for 6 hrs to cause cell damage before treatment with the aqueous *Graptopetalum* extract for 5 days. As shown in FIG. 7B, cells treated with the aqueous *Graptopetalum* extract survived better than those not. Therefore, the aqueous *Graptopetalum* extract of the present invention is safe to normal hepatocytes, and can even provide protection to hepatocytes against toxic chemicals.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

I claim:

1. A method of treating a subject suffering from or susceptible to a liver disease or medical condition, comprising administering an effective amount of a pharmaceutical composition comprising a water-soluble fraction of *Graptopetalum* to the subject, wherein the liver disease or medical condition is selected from the group consisting of liver inflammation, liver steatosis, liver fibrosis, liver cirrhosis, and hepatitis.

2. The method according to claim 1, wherein the water-soluble fraction of *Graptopetalum* is an aqueous *Graptopetalum* extract.

3. The method according to claim 1, wherein the *Graptopetalum* is *Graptopetalum paraguayense*.

4. The method according to claim 1, wherein the liver disease or medical condition is liver inflammation.

5. The method according to claim 1, wherein the liver disease or medical condition is liver steatosis.

6. The method according to claim 1, wherein the liver disease or medical condition is liver fibrosis.

7. The method according to claim 1, wherein the liver disease or medical condition is liver cirrhosis.

8. The method according to claim 1, wherein the liver disease or medical condition is hepatitis.

9. The method according to claim 8, wherein the hepatitis is hepatitis B.

10. The method according to claim 1, wherein the pharmaceutical composition is administered orally.

11. The method according to claim 2, wherein the aqueous *Graptopetalum* extract is prepared by:
   (a) freeze drying a whole *Graptopetalum* plant to form a dried *Graytopetalum* plant;
   (b) grinding the dried *Graptopetalum* plant to form a *Graptopetalum* powder;
   (c) lyophilizing the *Graptopetalum* powder to produce a lyophilized powder;
   (d) extracting the lyophilized powder with water to obtain a *Graptopetalum* extract; and
   (e) lyophilizing the *Graptopetalum* extract.

12. The method according to claim 11, wherein the *Graptopetalum* is *Graptopetalum paraguayense*.

13. The method according to claim 11, wherein the liver disease or medical condition is liver inflammation.

14. The method according to claim 11, wherein the liver disease or medical condition is liver steatosis.

15. The method according to claim 11, wherein the liver disease or medical condition is liver fibrosis.

16. The method according to claim 11, wherein the liver disease or medical condition is liver cirrhosis.

17. The method according to claim 11, wherein the liver disease or medical condition is hepatitis.

18. The method according to claim 17, wherein the hepatitis is hepatitis B.

19. The method according to claim 11, wherein the pharmaceutical composition is administered orally.

* * * * *